United States Patent [19]

deWalle et al.

[11] 4,403,510

[45] Sep. 13, 1983

[54] APPARATUS AND METHOD FOR ULTRASONIC INSPECTION

[76] Inventors: Stewart deWalle, 25 Lagos Rd., Rexdale, Ontario, Canada, M9W 4EJ; Dirk W. Hamoen, R.R. #3, Campbellville, Ontario, Canada, L0P 1B0; James W. Boyd, 36 Belvidere Ave., Hamilton, Ontario, Canada, L9A 3B7

[21] Appl. No.: 199,752

[22] Filed: Oct. 23, 1980

[51] Int. Cl.³ .......................................... G01N 29/04
[52] U.S. Cl. .................................................... 73/644
[58] Field of Search ................. 73/644, 642, 637, 638; 310/334–336

[56] References Cited

U.S. PATENT DOCUMENTS

| | | | |
|---|---|---|---|
| 3,255,626 | 6/1966 | Van Der Veer | 73/644 |
| 3,323,354 | 6/1967 | Daubresse | 73/644 |
| 3,420,097 | 1/1969 | Battermann et al. | 73/644 |
| 3,832,889 | 9/1974 | Bauer | 73/642 |
| 3,908,445 | 9/1975 | Verdon et al. | 73/644 |

FOREIGN PATENT DOCUMENTS 53-485  4/1977  Japan .............................. 73/644

*Primary Examiner*—Stephen A. Kreitman
*Attorney, Agent, or Firm*—Hirons, Rogers & Scott

[57] ABSTRACT

In a new method and apparatus for ultrasonic inspection of objects each inspection device of the apparatus is fed by gravity with a supply of a liquid coupling medium, from which the device produces a flowing liquid column that is directed at the object. The device mounts a focusing ultrasonic transducer that generates an ultrasonic beam in the liquid focused at a downstream point not less than about 5 cm from the oscillation generating surface. The external envelope of the ultrasonic beam is contained wholly within the external envelope of the liquid stream with a separation between them at least until the object is impinged by the liquid column. The liquid feed is made as non-turbulent and entrained bubble-free as possible to avoid the generation of unwanted background noise and spurious signals. The increase in distance through which inspection can be effected simplifies the application of the method to testing pipe wall and laminar thickness and to the testing of bulky bodies such as aeroplane wings. It also permits the application of the method and apparatus to the in situ testing of the wall thickness of well pipes.

14 Claims, 5 Drawing Figures

APPARATUS AND METHOD FOR ULTRASONIC INSPECTION

FIELD OF THE INVENTION

This invention is concerned with new apparatus for ultrasonic inspection and a new method employing such apparatus.

REVIEW OF THE PRIOR ART

The ultrasonic inspection of objects for the detection of flaws therein should now be considered a mature art. One of the principal problems that continues to concern those skilled in this art is the satisfactory acoustic coupling of the ultrasonic generator and detector (whether comprising separate transducer devices or a single combination transducer device) to the object under inspection, since this is the aspect of the art in which substantial improvements are believed to still be realisable. Owing to the high attenuation of acoustic waves in air, liquid coupling is used whenever possible, for example, by immersing the part of the object to be examined in the liquid coupling medium, or by producing a thin film of the liquid between the transducer and the surface of the object. Both of these prior methods suffer severe disadvantages, for example, the size of equipment required and the awkwardness involved in the immersion technique, and the difficulty of maintaining a uniform thin liquid film on a surface while the transducer moves over it.

One solution that has been employed successfully is described for example in U.S. Pat. No. 2,751,703, issued June 26, 1956 to Electrocurrents Inc. (D.C. Erdman). A stream or column of the liquid coupling medium is employed flowing in a direct line and forming an uninterrupted liquid bridge between the ultrasonic transducer and the test object, the stream carrying consecutively both the transmitted and the reflected signals. Erdman states that the length of the column can be between 0.75 mm and 150 cm (1/32 inch to 5 feet) but in the practice to date as it has developed since that proposal, the column is usually of the order of 6–12 mm in length, and a column of length 5 cm is considered very long. Attempts to use longer columns usually are not successful because of an accompanying increase in "background noise", to the extent that signals reflected from a flaw, etc. in the object are not readily detected.

The desire to use as long a column as possible arises from the need to inspect relatively large objects having considerable variations in their thickness dimensions, such as an aircraft wing, very thoroughly for flaws such as cracks and imperfect welds. Such an object must be scanned repeatedly along its length and width over a constantly changing surface contour and, unless the coupling column can be made sufficiently long to accomodate these changes, the mechanical scanning system required becomes so complex as to be uneconomic. Thus, with a sufficiently long coupling column available, back and forth motion of the object or the transducer in a flat plane is sufficient, and this is relatively easily obtained.

DEFINITION OF THE INVENTION

It is therefore an object of the invention to provide a new apparatus for ultrasonic inspection of the type employing a flowing column of coupling liquid for coupling an ultrasonic transducer and the surface of the device under test.

It is another object to provide a new method of ultrasonic inspection employing such apparatus.

In accordance with the present invention there is provided a new apparatus for ultrasonic inspection comprising:

an inspection device having a housing;

the housing having liquid inlet thereto, a liquid outlet therefrom, and passage means therein connecting the inlet and the outlet and for the production of a flowing liquid stream having an external envelope issuing from the outlet;

an ultrasonic transducer mounted in the housing so as to produce within the flowing liquid column a beam of ultrasonic oscillations having a respective external envelope;

the transducer focusing the said beam at a point downstream from itself, so that at least at its nearest point of impingement with an object to be inspected the ultrasonic beam envelope is contained wholly within the liquid column envelope.

Also in accordance with the invention there is provided a method of ultrasonic inspection including:

(a) generating from a supply thereof a flowing column of a liquid coupling medium having an external envelope;

(b) generating from a transducer a focused beam of ultrasonic oscillations within the liquid coupling medium, the beam having being focused so as to have an external envelope contained entirely within the liquid column envelope;

(c) directing the said stream and contained beam at the object to be inspected; and (d) examining ultrasonic oscillations reflected from the object and/or from inside the object.

DESCRIPTION OF THE DRAWINGS

Ultrasonic inspection apparatus and methods constituting particular preferred embodiments of the invention will now be described, by way of example, with reference in the accompanying diagrammatic drawing wherein.

DESCRIPTION OF THE PREFERRED EMBODIMENTS

Figure 1:
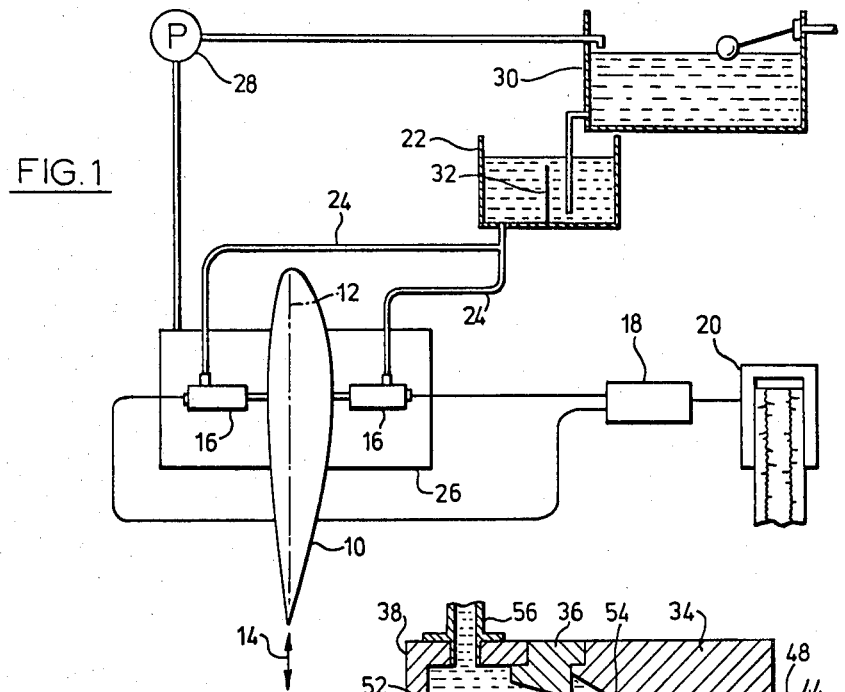
FIG. 1 is a schematic view of an apparatus of the invention adapted for the inspection of an aircraft wing as an example of a relatively large bulky object exhibiting considerable variation in its thickness dimensions.

Referring now to FIG. 1, the aircraft wing 10 to be inspected is mounted by any suitable mechanism (not shown) for back-and-forth horizontal motion in the plane 12, as indicated by the arrows 14. The mechanism will also provide for vertical movement of the wing at the end of each horizontal movement, so that successive horizontal movements cause scanning of different part of the wing surfaces.

The inspection apparatus consists of two oppositely disposed inspection devices 16 which are fed with appropriate electric signals from an electronic unit 18, and which return electric signals to the unit 18 for detection and analysis, the resultant output being displayed, for example, by a chart recorder 20. A single device 16 only can of course be used.

The two devices are also fed with a suitable coupling liquid under pressure. This pressure may, for example, be that of the standard water supply, or generated by a special pump unit. In the embodiment particularly illustrated by FIG. 1 it is generated by gravity from a quiescent supply tank 22 thereof via hoses 24, the used liquid being caught in a sump 26 and returned by a pump 28 to a level-controlled header supply tank 30 from which it flows again to the quiescent tank 22. It will be noted that the tank 22 contains a vertical weir 32 over which the liquid flows in passing from the header supply tank 30 to the devices 16, so that there is maximum opportunity for the liquid to become non-turbulent and to give up entrained air bubbles.

Figure 2:
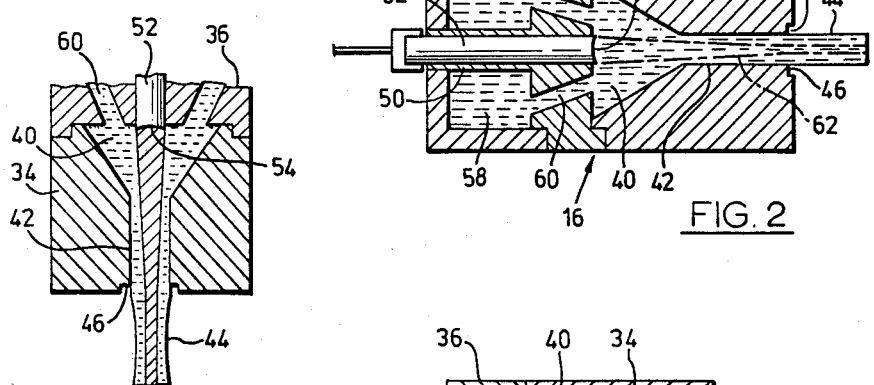
FIG. 2 is a longitudinal cross-section through an inspection device of the invention comprising a transducer and means for generating the required column of coupling liquid.

Referring now to FIG. 2, each inspection device 16 is in this embodiment assembled from three major component parts 34, 36 and 38 which are arranged to spigot into one another. The "front" part 34 has a frusto-conical chamber 40 therein the apex of which discharges into an axial bore 42 of uniform cross-section, so that the liquid passing therein is collimated into a correspondingly uniform cylindrical cross-section column or stream 44 that issues from an outlet 46 in the "front" face of the part 34. This column or stream should be as coherent and non-turbulent as possible, that is to say it should have the minimum tendency to splash and for droplets and spray to separate therefrom. The outlet orifice is located in a counterbore 48 in the front face so that chance impacts of that face, for example, against the object being inspected, will not damage the edge of the orifice with consequent disruption of the collimated liquid stream.

The "middle" part 36 is of approximate "T" cross-section with the leg 50 thereof forming an elongated spigot having an ultrasonic transducer 52 accommodated in a bore therein, so that its "front" end surface 54 protrudes into the chamber 50 and will direct the ultrasonic beam into the bore 42 coaxially therewith. The "rear" part 38 provides a liquid inlet 56 and inlet chamber 58 surrounding the spigot 50, the chamber 58 feeding to the chamber 40 via a plurality of circumferentially-disposed bores 60. The flow cross-sectional area of the passage means in the housing from the inlet 56 to the outlet 46 decreases progressively, so as to avoid any possibility of the production of turbulent flow, which increases spurious ultrasonic reflections in the liquid stream and makes the detection of flaw echoes more difficult. A ratio of at least 2:1 in reduction is preferred.

It will be noted that the transducer surface 54 is concave and this will result in the emitted ultrasonic oscillations being focused at a point downstream of the surface. This focus distance should be of the order of 12.5–15 cm for optimum performance and should not in any case be less than 5 cm. It is found surprisingly that the ultrasonic beam reduces in cross-sectional area from the surface 54 to the focus point and thereafter continues as a parallel collimated beam totally enclosed within the liquid stream; the typical external "envelope" 62 of the ultrasonic beam is shown in broken lines in FIGS. 2 through 4. It is now found possible to project the stream 44 for much greater distances than has been possible hitherto, without excessive production of spurious and background signals that will otherwise obscure the wanted echo signals representative of a fault. Thus, it is now found possible to permit distances vertically, up or down, for about 50 cm, and horizontally for about 15 cm, between the outlet 46 and the surface under test, whereas previously distances of as small as 5 cm resulted in unreliable results.

Figure 3:
FIG. 3 is part cross-section of the device of FIG. 2 to illustrate its operation with a vertically-downward flowing column of liquid.
Figure 4:
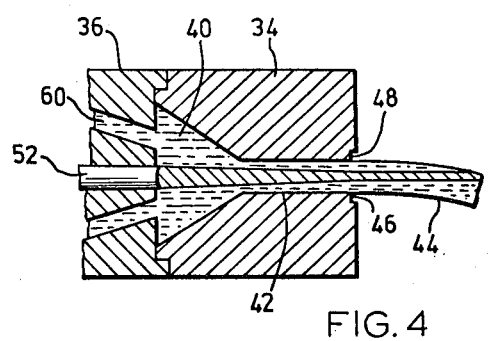
FIG. 4 is a part cross-section similar to FIG. 3 to illustrate its operation with a horizontally-flowing liquid column and FIG. 5 is a schematic cross-section to illustrate the apparatus and method of the invention applied to the in situ testing of the wall thickness of a well casing pipe.

It is found essential that the external envelope of the ultrasonic beam stay entirely within the correspondingly external "envelope" of the liquid stream with no interference between them. No difficulty is encountered when the liquid stream is directed vertically downward, as illustrated by FIG. 3, or upward, but there may be a problem when the liquid stream is directed horizontally, as illustrated by FIGS. 1 and 4. Thus, the liquid stream curves downward as it exits from the inspection device, while the ultrasonic beam continues in a straight line and, with the longer distances that are possible with this invention, there is the possibility of the envelopes interfering before the object is encountered, as shown in FIG. 4. One solution is to increase the pressure of the liquid in order to increase the distance before the downard curvature causes such interference; another solution not illustrated is to offset the transducer downward, so that the ultrasonic beam can travel further before the envelopes interfere.

A wide range of ultrasonic frequencies is used for inspection purposes, the most popular being the range 2.25–5 Megahertz. While in prior art apparatus known to us difficulties are experienced if frequencies higher than 5 MHz are employed it is found with the apparatus of this invention that it is entirely possible to use transducers operating at frequencies as high as 25 MHz. These higher frequencies are possible because of the reduced thickness of the water stream. It has been found that higher frequencies can be employed effectively if care is taken, as with the apparatus and method of the invention, to avoid turbulence in the liquid flow and also to avoid the formation of bubbles within the liquid. Such turbulence eddies and bubbles act as reflectors producing the undesired background echoes, and this effect increases with increase of frequency. It is found with the apparatus of the invention that the reduction is even more effective than was anticipated, and it is postulated that this may be due to the fact that such eddies and bubbles tend by vortex action to accumulate in the radially outer part of the liquid stream, so that there are correspondingly less in the central part of the stream through which the ultrasonic beam passes. It is further found surprisingly that satisfactory testing is still obtained when the body under test is at a relatively high temperature, e.g. up to about 325° C., well above the boiling point of the coupling water.

Figure 5:
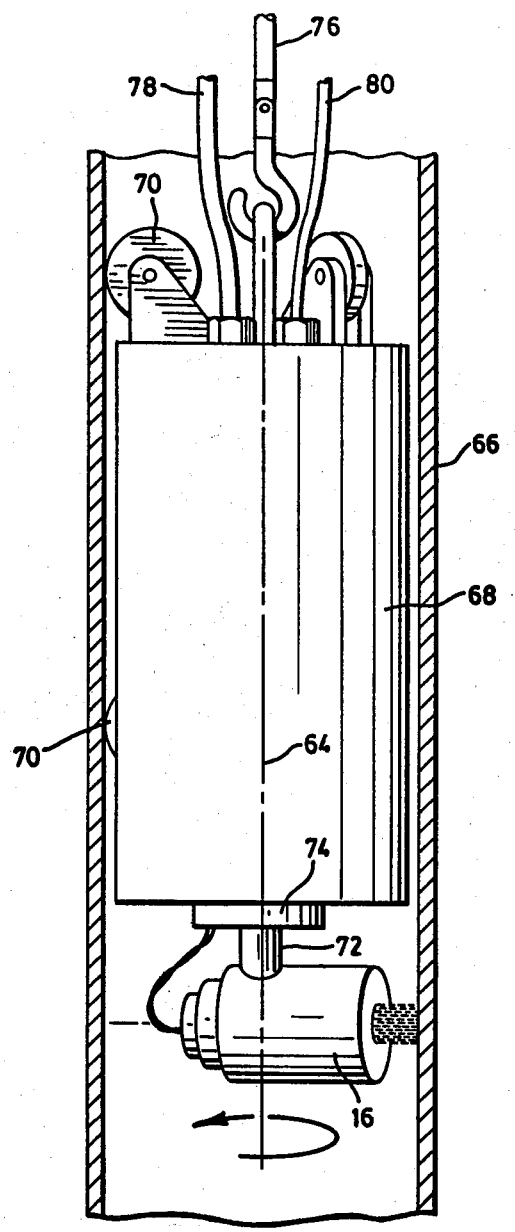

The application of the invention to the testing of the thickness of the wall of a pipe by an externally mounted transducer, as well as to the testing of the thickness of a lamination will be apparent to those skilled in the art. FIG. 5 illustrates the application of the invention to the in situ testing of the thickness of the wall of a well casing pipe. Such pipes are very subject to corrosion and consequent perforation of the pipe wall, so that simple and inexpensive methods of checking are highly desirable. The inspection device 16 is mounted for rotation about the longitudinal axis 64 of a well casing pipe 66 by a support body 68 which itself is designed to run inside the pipe 66 with wheels 70 engaging the inside pipe wall. The coupling liquid is supplied to the device 16 via a swivelling connecting pipe 72, while electric power is supplied via a slip ring assembly 74. The device is lowered and raised by a hoist cable 76 and water and electric power supplied from the surface via flexible connections 78 and 80 respectively, the latter also serving to return the signals from the device 16 to the surface.

We claim:

1. Apparatus for ultrasonic inspection of an object comprising:
   an inspection device having a housing;
   the housing having a liquid inlet thereto, a liquid outlet therefrom, and passage means therein connecting the inlet and the outlet and including a convergent portion for the production of a substantially non-turbulent flowing liquid column having an external envelope issuing from the outlet;
   an ultrasonic transducer mounted in the housing so as to produce within the flowing liquid column a beam of ultrasonic oscillations having a respective external envelope;
   the transducer focusing the said beam at a point downstream from itself, so that the cross sectional area of the beam is less than the cross sectional area of the column generated at said outlet whereby upon impingement with an object to be inspected the ultrasonic beam envelope is contained wholly within the liquid column and noise caused by turbulence on the surface of the column is inhibited.

2. Apparatus as claimed in claim 1, wherein the transducer focus point is not less than 5 cm from the oscillation emitting surface of the transducer.

3. Apparatus as claimed in claim 2, wherein the transducer focus point is between about 12.5 and 15.0 cm from the transducer oscillation emitting surface.

4. Apparatus as claimed in claim 1, wherein the said passage means are of progressively smaller flow cross-section from said inlet to said outlet to avoid turbulence in the flow of liquid therein.

5. Apparatus as claimed in claim 4, wherein the reduction in flow cross-section within the passage means to the said outlet is greater than 2:1.

6. Apparatus as claimed in claim 1, wherein means for feeding coupling liquid to the said device inlet comprise a quiescent supply tank thereof from which the liquid is fed by gravity to the inlet.

7. Apparatus as claimed in claim 6, wherein the said quiescent supply tank includes a weir over which liquid therein flows in its passage from the tank inlet to the tank outlet.

8. Apparatus according to claim 1 wherein said transducer is supported in said passage means between said inlet and outlet by a partition and communication between said inlet and outlet is provided by bores in said partition equally spaced around said transducer.

9. Apparatus according to claim 1 wherein the axis of said inlet is substantially perpendicular to the axis of said outlet.

10. A method for the ultrasonic inspection of an object including the steps of;
    (a) generating from a convergent nozzle a substantially non turbulent flowing column of a liquid coupling medium having an external envelope;
    (b) generating from a transducer a focused beam of ultrasonic oscillations wthin the liquid coupling medium, the beam being focused at a point downstream from the transducer so as to have a cross section less than the cross section of the nozzle and be contained entirely within the liquid column envelope;
    (c) directing the said column and contained beam at the object to be inspected; and
    (d) examining ultrasonic oscillations received by a receiver from the object and/or from inside the object.

11. A method as claimed in claim 10, wherein the transducer focus point is not less than 5 cm from the oscillation emitting surface of the transducer.

12. A method as claimed in claim 11, wherein the transducer focus point is between about 12.5 and 15.0 cm from the transducer oscillation emitting surface.

13. A method as claimed in claim 10, wherein means for feeding coupling liquid to the said device inlet comprise a quiescent supply tank thereof from which the liquid is fed by gravity to the inlet.

14. A method as claimed in claim 13, wherein the said quiescent supply tank includes a weir over which liquid therein flows in its passage from the tank inlet to the tank outlet.

* * * * *